# (12) United States Patent
Serebryany et al.

(10) Patent No.: US 8,895,723 B2
(45) Date of Patent: Nov. 25, 2014

(54) METHODS OF PREPARING SUBSTITUTED NUCLEOTIDE ANALOGS

(71) Applicants: Alios BioPharma, Inc., South San Francisco, CA (US); Vertex Pharmaceuticals Inc., Cambridge, MA (US)

(72) Inventors: Vladimir Serebryany, Burlingame, CA (US); Jyanwei Liu, Sunnyvale, CA (US); Leonid Beigelman, San Mateo, CA (US); Young Chun Jung, Lexington, MA (US); Peter Jamison Rose, Littleton, MA (US); Shereen Ibrahim, Cambridge, MA (US); Cavan McKeon Bligh, Somerville, MA (US); Luigi Anzalone, West Chester, PA (US)

(73) Assignees: Alios BioPharma, Inc., South San Francisco, CA (US); Vertex Pharmaceuticals Inc., Cambridge, MA (US)

(*) Notice: Subject to any disclaimer, the term of this patent is extended or adjusted under 35 U.S.C. 154(b) by 0 days.

(21) Appl. No.: 13/845,415

(22) Filed: Mar. 18, 2013

(65) Prior Publication Data

US 2013/0281687 A1    Oct. 24, 2013

Related U.S. Application Data

(60) Provisional application No. 61/734,564, filed on Dec. 7, 2012, provisional application No. 61/613,758, filed on Mar. 21, 2012.

(51) Int. Cl.
| | | |
|---|---|---|
| C07H 21/00 | (2006.01) | |
| C07H 19/10 | (2006.01) | |
| C07F 9/26 | (2006.01) | |
| C07F 9/6558 | (2006.01) | |
| C07H 1/00 | (2006.01) | |
| C07F 9/6506 | (2006.01) | |

(52) U.S. Cl.
CPC   *C07H 19/10* (2013.01); *C07F 9/26* (2013.01); *C07F 9/65586* (2013.01); *C07H 1/00* (2013.01); *C07F 9/65061* (2013.01)

USPC ............... 536/25.33; 536/25.3; 540/1; 540/2; 540/5

(58) Field of Classification Search
None
See application file for complete search history.

(56) References Cited

U.S. PATENT DOCUMENTS

| | | |
|---|---|---|
| 2012/0070411 A1 | 3/2012 | Beigelman et al. |
| 2012/0070415 A1 | 3/2012 | Beigelman et al. |
| 2012/0071434 A1 | 3/2012 | Smith et al. |
| 2012/0165286 A1 | 6/2012 | Beigelman et al. |
| 2013/0164261 A1 | 6/2013 | Wang et al. |
| 2013/0165400 A1 | 6/2013 | Beigelman et al. |
| 2013/0252920 A1 | 9/2013 | Blatt et al. |
| 2013/0253181 A1 | 9/2013 | Serebryany et al. |

FOREIGN PATENT DOCUMENTS

| | | |
|---|---|---|
| WO | WO 2010/108140 A1 | 9/2010 |
| WO | WO 2012/040127 | 3/2012 |
| WO | WO 2013/142124 | 9/2013 |
| WO | WO 2013/142159 | 9/2013 |
| WO | WO 2013/142525 | 9/2013 |

OTHER PUBLICATIONS

Miao, et al, ""One Pot Synthesis of Aryl Thiophosphoramidate Derivatives of AZT."" *Synthetic Communications*, 2002, 32(21), 3301-3309.
International Search Report and Written Opinion issued on Apr. 8, 2013 in the corresponding PCT Application No. PCT/US2013/030285, filed on Mar. 11, 2013.
Greene et al., Protective Groups in Organic Synthesis, 3. Ed., John Wiley & Sons, (1999) Cover & Contents pages.
McOmie, Protective Groups in Organic Chemistry, Plenum Press (1973), Cover & Contents pages only.
White et al., ""Integration of supercritical fluid chromatography into drug discovery as a routine support tool: II. Investigation and evaluation of supercritical fluid chromatography for achiral batch purification,"" *Journal of Chromatography A* (May 13, 2005) 1074:175-185.

*Primary Examiner* — Patrick Lewis
(74) *Attorney, Agent, or Firm* — Knobbe Martens Olson & Bear LLP

(57) ABSTRACT

Disclosed herein are methods of preparing a phosphorothioate nucleotide analog, which are useful in treating diseases and/or conditions such as viral infections.

20 Claims, 3 Drawing Sheets"

METHODS OF PREPARING SUBSTITUTED NUCLEOTIDE ANALOGS

INCORPORATION BY REFERENCE TO ANY PRIORITY APPLICATIONS

Any and all applications for which a foreign or domestic priority claim is identified in the Application Data Sheet as filed with the present application, are hereby incorporated by reference under 37 CFR 1.57., and includes U.S. provisional application Nos. 61/613,758, filed Mar. 21, 2012 and 61/734, 564, filed Dec. 7, 2012.

PARTIES OF JOINT RESEARCH AGREEMENT

The claimed subject matter of the present application was made by or on behalf of parties to a joint research agreement that was in effect on or before the date the claimed subject matter was made; the claimed subject matter was made as a result of activities undertaken within the scope of the joint research agreement; and the parties to the joint research agreement include: Alios BioPharma, Inc., Vertex Pharmaceuticals Inc., and Vertex Pharmaceuticals (Switzerland) LLC.

The joint research agreement was a written contract, grant or cooperative agreement entered into by the above-mentioned parties for the performance of experimental, developmental or research work in the field of the claimed subject matter, and executed on Jun. 13, 2011.

BACKGROUND

1. Field

The present application relates to the fields of chemistry, biochemistry, and medicine. More particularly, disclosed herein are methods of preparing a phosphorothioate nucleotide analog, which can be useful in treating diseases and/or conditions such as viral infections.

2. Description

Nucleoside analogs are a class of compounds that have been shown to exert antiviral and anticancer activity both in vitro and in vivo, and thus, have been the subject of widespread research for the treatment of viral infections and cancer. Nucleoside analogs are usually therapeutically inactive compounds that are converted by host or viral enzymes to their respective active anti-metabolites, which, in turn, may inhibit polymerases involved in viral or cell proliferation. The activation occurs by a variety of mechanisms, such as the addition of one or more phosphate groups and, or in combination with, other metabolic processes.

SUMMARY

Some embodiments disclosed herein relate to a method of preparing a compound of Formula (I), or a pharmaceutically acceptable salt thereof. Some embodiments disclosed herein relate to a method of preparing a compound of Formula (I)(i) and/or a compound of Formula (I)(ii), or a pharmaceutically acceptable salt thereof.

Some embodiments disclosed herein relate to a method of preparing compound 2.

DETAILED DESCRIPTION

Figure 1:
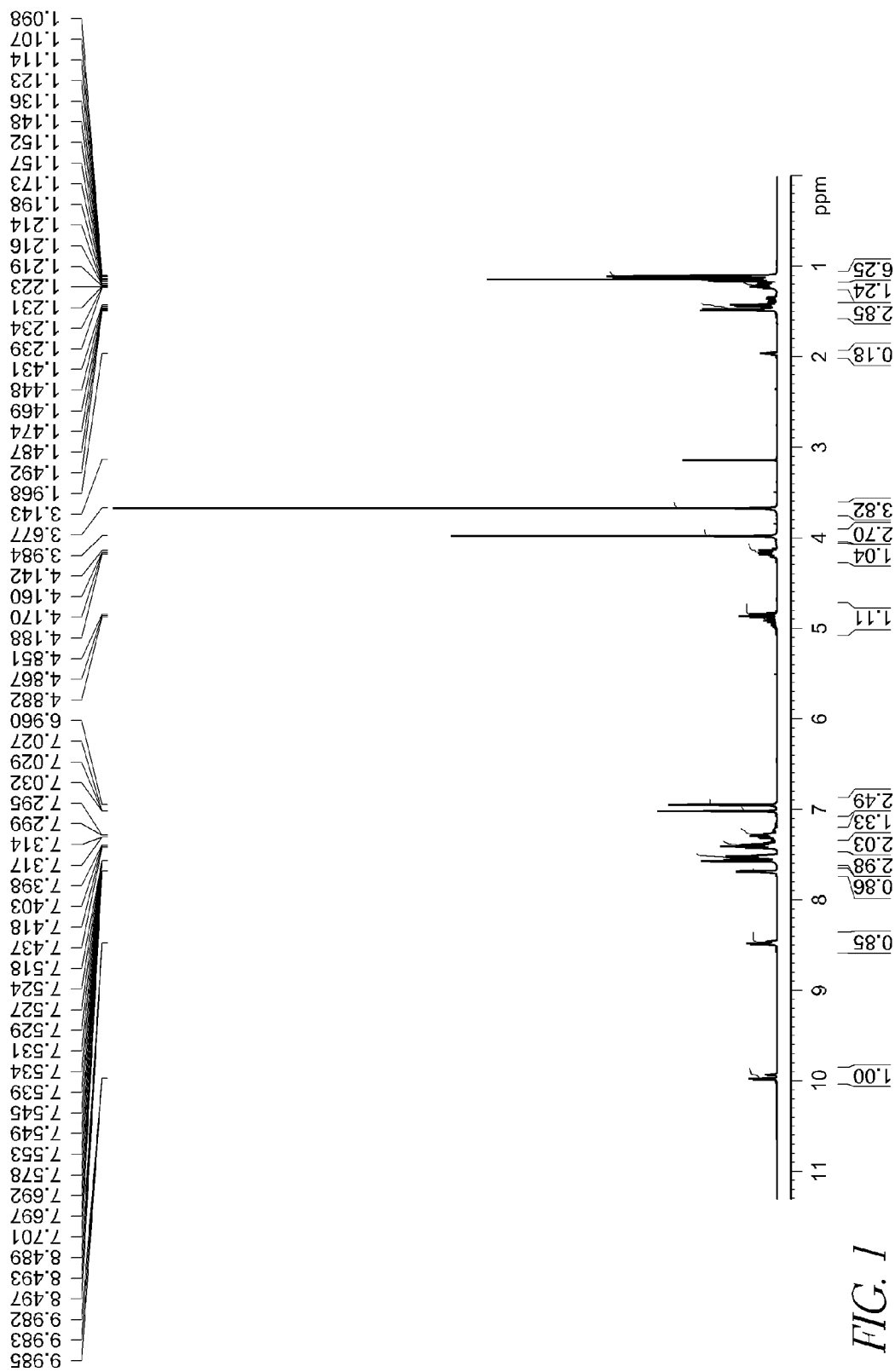
FIG. 1 shows $^1$H NMR spectrum of a diastereomeric mixture of compound (C)(i) and compound (C)(ii).

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, and hexyl. The alkyl group may be substituted or unsubstituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene, and azulene. An aryl group may be substituted or unsubstituted.

As used herein, "amine" refers to a compound of the formula $NR^AR^B$, wherein $R^A$ and $R^B$ are independently hydrogen, optionally substituted alkyl or an optionally substituted aryl. The term amine includes primary amines, secondary amines and tertiary amines.

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more the indicated substituents. If no substituents are indicated, it is meant that the indicated "optionally substituted" or "substituted" group may be substituted with one or more group(s) individually and independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxyl, alkoxy, aryloxy, acyl, mercapto, alkylthio, arylthio, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group, and protected derivatives thereof.

The terms "protecting group" and "protecting groups" as used herein refer to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis*, 3. Ed. John Wiley & Sons, 1999, and in J. F. W. McOmie, *Protective Groups in Organic Chemistry Plenum Press*, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl; substituted benzyl; alkylcarbonyls and alkoxycarbonyls (e.g., t-butoxycarbonyl (BOC), acetyl, or isobutyryl); arylalkylcarbonyls and arylalkoxycarbonyls (e.g., benzyloxycarbonyl); substituted methyl ether (e.g. methoxymethyl ether); substituted ethyl ether; a substituted benzyl ether; tetrahydropyranyl ether; silyls (e.g., trimethylsilyl, triethylsilyl, triisopropylsilyl, t-butyldimethylsilyl, tri-iso-propylsilyloxymethyl, [2-(trimethylsilyl)ethoxy]methyl or t-butyldiphenylsilyl); esters (e.g., benzoate ester); carbonates (e.g., methoxymethylcarbonate); sulfonates (e.g., tosylate or mesylate); acyclic ketal (e.g., dimethyl acetal); cyclic ketals (e.g., 1,3-dioxane, 1,3-dioxolanes, and those described herein); acyclic acetal; cyclic acetal (e.g., those described herein); acyclic hemiacetal; cyclic hemiacetal; cyclic dithioketals (e.g., 1,3-dithiane or 1,3-dithiolane); orthoesters (e.g., those described herein) and triarylmethyl groups (e.g., trityl; monomethoxytrityl (MMTr); 4,4'-dimethoxytrityl (DMTr); 4,4',4''-trimethoxytrityl (TMTr); and those described herein).

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid, and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluensulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. In addition, the term "comprising" is to be interpreted synonymously with the phrases "having at least" or "including at least". When used in the context of a process, the term "comprising" means that the process includes at least the recited steps, but may include additional steps. When used in the context of a compound, composition, or device, the term "comprising" means that the compound, composition, or device includes at least the recited features or components, but may also include additional features or components. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof.

Likewise, it is understood that, in any compound described, all tautomeric forms are also intended to be included. For example all tautomers of a phosphate and a phosphorothioate groups are intended to be included. Examples of tautomers of a phosphorothioate include the following:

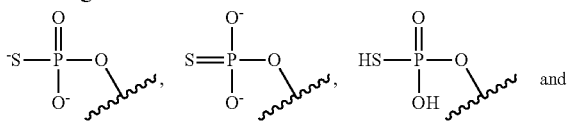

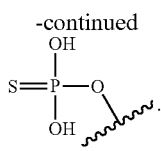

Furthermore, all tautomers of heterocyclic bases known in the art are intended to be included, including tautomers of natural and non-natural purine-bases and pyrimidine-bases.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

It is understood that the methods and combinations described herein include crystalline forms (also known as polymorphs, which include the different crystal packing arrangements of the same elemental composition of a compound), amorphous phases, salts, solvates, and hydrates. In some embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

Where a range of values is provided, it is understood that the upper and lower limit, and each intervening value between the upper and lower limit of the range is encompassed within the embodiments.

Some embodiments disclosed herein relate to a method of preparing a compound of Formula (I), or a pharmaceutically acceptable salt thereof:

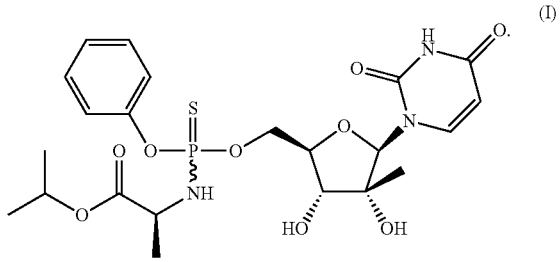 [SMILES: CC(C)OC(=O)[C@H](C)NP(=S)(OC[C@H]1O[C@@H](n2ccc(=O)[nH]c2=O)[C@](C)(O)[C@@H]1O)Oc1ccccc1]

In some embodiments, a method of preparing a compound of Formula (I) can include coupling a compound of Formula (A) and a compound of Formula (B), wherein the —OH groups and —NH group of the compound of Formula (A) are unprotected during the coupling reaction:

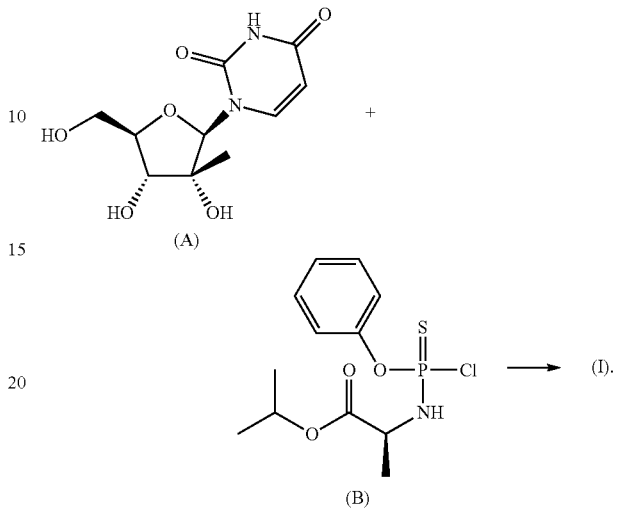

In some embodiments, a compound of Formula (I) can be obtained as a single diastereomer. In other embodiments, a compound of Formula (I) can be obtained as a mixture of diastereomers, for example (I)

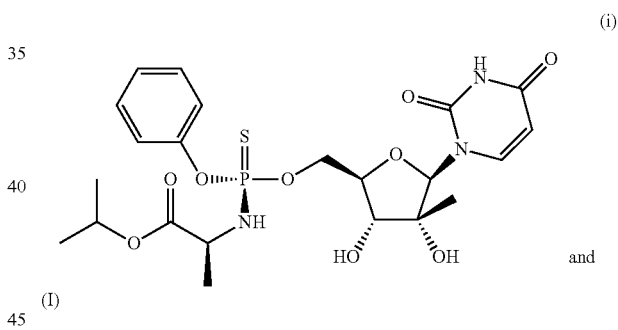

(I)

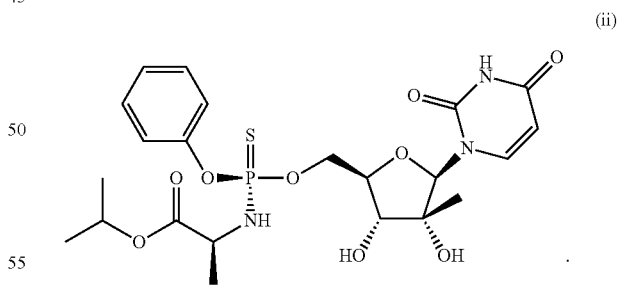

In some embodiments, a compound of Formula (I) can be a 1:1 mixture of two diastereomers, such as those described herein (for example, a compound of Formula (I)(i) and a compound of Formula (I)(ii)). In some embodiments, a compound of Formula (I) can be diastereomerically enriched (for example, one diastereomer can be present at an amount of >55% (eq.), ≥75% (eq.), ≥80% (eq.), ≥90% (eq.), ≥95% (eq.), ≥98% (eq.), or ≥99% (eq.) in the mixture as compared to any other diastereomers present. In some embodiments, a compound of Formula (I) can be diastereomerically enriched in a compound of Formula (I)(i). In others embodiments, a compound of Formula (I) can be diastereomerically enriched in a compound of Formula (I)(ii), e.g., >55% (eq.), ≥75% (eq.), ≥80% (eq.), ≥90% (eq.), ≥95% (eq.), ≥98% (eq.), or ≥99% (eq.).

In some embodiments, neutralizing the charge on the thiophosphate group may facilitate the penetration of the cell membrane by a compound of Formula (I), or a pharmaceutically acceptable salt thereof (including compound of Formula (I)(i) and Formula (I)(ii), or a pharmaceutically acceptable salt of the aforementioned) by making the compound more lipophilic compared to a thionucleotide having a comparable structure with one or more charges present on the thiophosphate. Once absorbed and taken inside the cell, the groups attached to the thiophosphate can be easily removed by esterases, proteases, or other enzymes. In some embodiments, the groups attached to the thiophosphate can be removed by simple hydrolysis. Inside the cell, the thio-monophosphate thus released may then be metabolized by cellular enzymes to the thio-diphosphate or the active thio-triphosphate. In some embodiments, the phosphorylation of a thio-monophosphate of a compound of Formula (I), or pharmaceutically acceptable salt thereof, can be stereoselective. For example, a thio-monophosphate of a compound of Formula (I) (including a compound of Formula (I)(i) and a compound of Formula (I)(ii)) can be phosphorylated to give an alpha-thiodiphosphate and/or an alpha-thiotriphosphate compound that can be enriched in the (R) or (S) diastereomer with respect to the 5'-O-phosphorous atom.

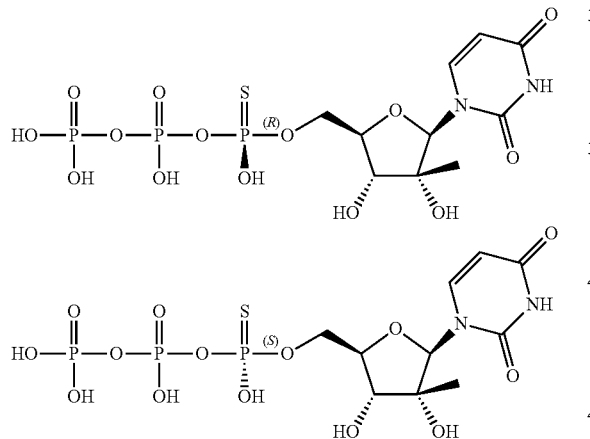

For example, one of the (R) and (S) configuration with respect to the 5'-O-phosphorous atom of the alpha-thiodiphosphate and/or the alpha-thiotriphosphate compound can be present in an amount >50%, ≥75%, ≥90%, ≥95% or ≥99% compared to the amount of the other of the (R) or (S) configuration with respect to the 5'-O-phosphorous atom. In some embodiments, phosphorylation of a compound of Formula (I), or pharmaceutically acceptable salt thereof, can result in the formation of a compound that has the (R)-configuration at the 5'-O-phosphorous atom. In some embodiments, phosphorylation of a compound of Formula (I), or pharmaceutically acceptable salt thereof, can result in formation of a compound that has the (S)-configuration at the 5'-O-phosphorous atom.

Synthesis

General synthetic routes to prepare the compound of Formula (I), and some examples of starting materials used to synthesize the compounds of Formula (I) are shown in Scheme 1, and described herein. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

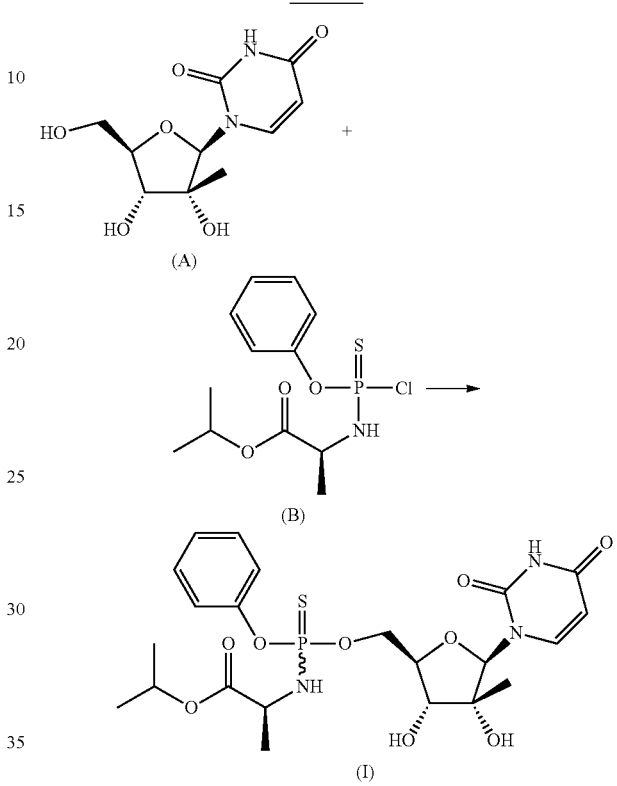

Scheme 1

One method for forming a compound of Formula (I) is shown in Scheme 1. A variety of methods can be used in the reaction between a compound of Formula (A) and a compound of Formula (B). In some embodiments, a compound of Formula (A) can be coupled to a compound of Formula (B) using a base, an acid or a Grignard reagent. In some embodiments, to facilitate the coupling, a Grignard reagent can be used. Suitable Grignard reagents are known to those skilled in the art and include, but are not limited to, alkylmagnesium chlorides and alkylmagnesium bromides. In some embodiments, the Grignard reagent can have the general formula of $R^C$—MgBr or $R^C$—MgCl, wherein $R^C$ can be an optionally substituted alkyl or an optionally substituted aryl. In some embodiments, a reaction between a compound of Formula (A) and a compound of Formula (B) can be conducted in the presence of a base. For example, a compound of Formula (B) can be added to a mixture of a compound of Formula (A) and a base. Examples of bases include, but are not limited to, an optionally substituted amine base, such as an alkylamine (including mono-, di- and tri-alkylamines (for example, monoethylamine, diethylamine and triethylamine)), optionally substituted pyridines (such as collidine) and optionally substituted imidazoles (for example, N-methylimidazole)). In some embodiments, a reaction between a compound of Formula (A) and a compound of Formula (B) can be conducted in the presence of N-methylimidazole. In some embodiments, a reaction between a compound of Formula (A) and a compound of Formula (B) can be conducted in the presence of an acid. Example of a suitable acid is trifluoromethanesulfonic acid.

A Grignard reagent can react with a compound of Formula (A) to form an alkoxide at the 5'-position of a compound of Formula (A). The alkoxide attached to the 5'-position of a compound of Formula (A) can react with a compound of Formula (B) to form a compound of Formula (I). A base, such as N-methyl imidazole (NMI), can displace the chloride of a compound of Formula (B) to form an intermediate. This intermediate can react with a compound of Formula (A) to form a compound of Formula (I), wherein the same base or a different base can assist in the reaction through the removal of the hydrogen of the hydroxy group attached to the 5'-position of the compound of Formula (A). When the base is NMI, a compound of Formula (C) can be formed, wherein the counterion is a chloride anion.

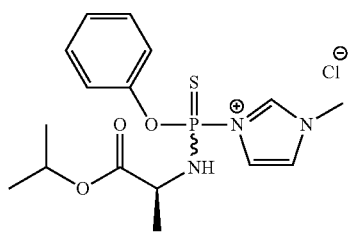

(C)

The amount of base used for the reaction between a compound of Formula (A) and a compound of Formula (B) can be varied. In some embodiments, the amount of a base can be present in more than a catalytic amount. In some embodiments, the amount of a base can be ≥3 equivalent compared to the amount of a compound of Formula (B) (≥3 eq.:1 eg. of base:a compound of Formula (B)). In some embodiments, the amount of a base can be in the range of about 2 equivalents to about 5 equivalents to the amount of a compound of Formula (B) (≥2-5 eq.:1 eq. of base:a compound of Formula (B)). In some embodiments, the amount of a base can be about 3 equivalents to the amount of a compound of Formula (B) (≥3 eq.:1 eq. of base:a compound of Formula (B)). In some embodiments, the amount of a base and the amount of a compound of Formula (B) can be approximately the same (1 eq.: 1 eq. of base:a compound of Formula (B)). When the amount of a base is in excess compared to the amount of a compound of the Formula (B), the base can facilitate the reaction by removing hydrogen chloride generated in the reaction.

Scheme 2

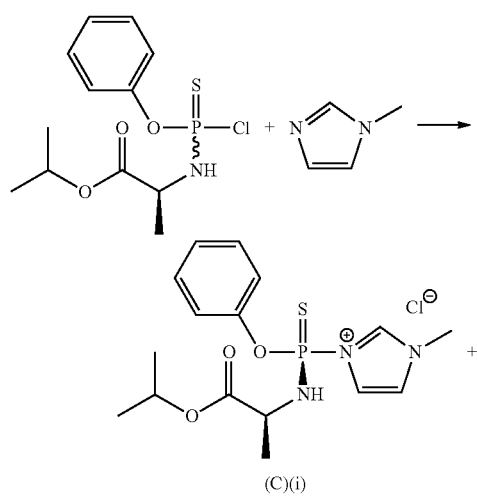

(C)(i)

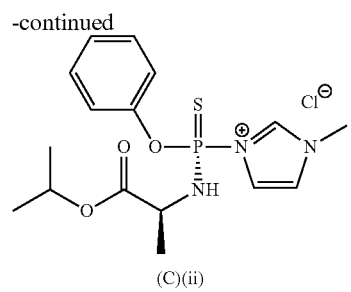

(C)(ii)

In some embodiments, the reaction between a compound of Formula (B) and a base can provide a diastereomeric mixture of a compound of Formula (C)(i) and a compound of Formula (C)(ii). In some embodiments, the reaction between a compound of Formula (B) and a base can provide a compound of Formula (C) that can be enriched in one diastereomer, for example, the (S)-diastereomer with respect to the phosphorous (Compound C(ii)). In some embodiments, a reaction between a compound of Formula (B) and a base (such as NMI) as described herein can provide a compound of Formula (C) that can be ≥60%, ≥75%, ≥90% enriched in the (S)-diastereomer with respect to the phosphorous. In some embodiments, a reaction between a compound of Formula (B) and a base (such as NMI) as described herein can provide a diastereomeric mixture with a diastereomeric ratio of 2 or more:1 of a compound of Formula (C)(ii) to a compound of Formula (C)(i) (a compound of Formula (C)(ii):a compound of Formula (C)(i)). In other embodiments, the reaction between a compound of Formula (B) and a base can provide a compound of Formula (C) that can be enriched in the (R)-diastereomer with respect to the phosphorous (Compound C(i)). In other embodiments, a reaction between a compound of Formula (B) and a base (such as NMI) as described herein can provide a compound of Formula (C) that can be ≥60%, ≥75%, ≥90% enriched in the (R)-diastereomer with respect to the phosphorous. In other embodiments, a reaction between a compound of Formula (B) and a base (such as NMI) as described herein can provide a diastereomeric mixture with a diastereomeric ratio of 2 or more:1 of a compound of Formula (C)(i) to a compound of Formula (C)(ii) (a compound of Formula (C)(i):a compound of Formula (C)(ii)).

Scheme 3

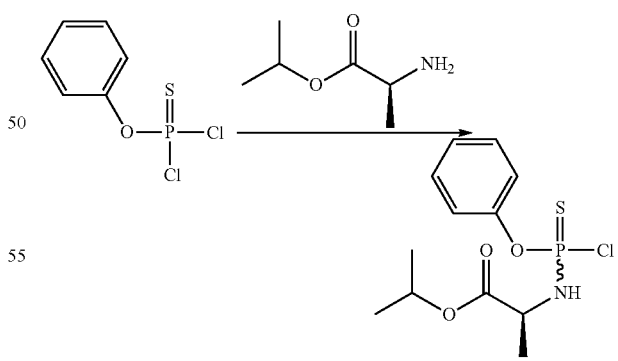

Various methods and reagents can be used to prepare a compound of Formula (B). One suitable method is shown in Scheme 3. As shown in Scheme 3, O-phenylphosphorodichloridothioate can be reacted with (S)-isopropyl 2-aminopropanote. In some embodiments, the (S)-isopropyl 2-aminopropanote can be in free base form. In other embodiments, (S)-isopropyl 2-aminopropanote can be a salt form. In some embodiments, the (S)-isopropyl 2-aminopropanote salt can be a HCl salt. In other embodiments, (S)-isopropyl 2-aminopropanote can be a methanesulfonic acid salt. Methods for preparing a compound of Formula (B) can also include the use of a base, such as those described herein. In some embodiments, the base can be triethylamine. Additionally, the reaction can take place in a solvent. Suitable solvents include, but are not limited to, non-polar solvents. Examples of non-polar solvents include the following: hexane, benzene, toluene, 1,4-dioxane, chloroform, dichloromethane and diethyl ether.

An advantage of the synthesis shown in Scheme 1 is that it is not necessary to protect one more hydroxy groups (such as the hydroxy groups attached to the 2'-position and the 3'-position of the pentose ring) and/or one or more amine groups (for example, on the uracil) of the compound of Formula (A) prior to coupling to the compound of Formula (B). Protecting groups, for example, protecting groups on the oxygens at the 2'-position and/or 3'-position of the pentose ring, and/or on the amine of the uracil, can be used to minimize the formation of undesirable amounts of side reaction byproduct(s). However, use of protecting groups increases the number of steps in the formation of the desired product and can decrease the overall yield of the desired product. The synthesis shown in Scheme 1 can result in a higher yield of the desired product and/or fewer reaction steps, as protection and deprotection steps are not included.

The ratio of a compound of Formula (A) to a compound of Formula (B) can be varied. In some embodiments, the amount of a compound of Formula (B) can be present in excess compared to the compound of Formula (A), e.g., 1.15 eq. or greater (or, alternatively, a molar ratio of Formula (A) to Formula (B) of 1.0:(1.15 or greater)). In some embodiments, even higher excesses of the compound of Formula (B) are employed, e.g., 1.2, 1.3, 1.4, 1.5, 1.6, 1.7, 1.8, 1.9, or 2.0 or more eq. relative to Formula (A). In some embodiments, the equivalents of compound of Formula (B) relative to the equivalents to Formula (A) can be in the range of 1.0 eq.:1.0 eq. to 2.0 eq.:1.0 eq. (for example in the range of 1.3 eq.:1.0 eq. to 1.6 eq.:1.0 eq.). In some embodiments, the amount of a compound of Formula (A) can be present in excess compared to the compound of Formula (B), e.g., 1.15 eq. or greater. In some embodiments, even higher excesses of the compound of Formula (A) can be employed, e.g., 1.2, 1.3, 1.4, 1.5, 1.6, 1.7, 1.8, 1.9, or 2.0 or more eq. In some embodiments, the higher excess of a compound of Formula (B) can improve the selective formation of the compound of Formula (I)(ii) compared to the compound of Formula (I)(i).

The reaction between a compound of Formula (A) and a compound of Formula (B) can be conducted in one solvent or a mixture of two or more solvents. In some embodiments, the reaction between a compound of Formula (A) and a compound of Formula (B) can be conducted using a polar aprotic solvent. Examples of polar aprotic solvents include, but are not limited to, dimethylformamide, tetrahydrofuran, ethyl acetate, acetone, acetonitrile, dimethyl sulfoxide or methyl isobutyl ketone). In some embodiments, the solvent can be acetonitrile (ACN). In some embodiments, the solvent can be methyl isobutyl ketone (MIBK).

In some embodiments, a compound of Formula (I) can be partitioned between an organic phase (e.g., an acetate, such as ethyl acetate or isopropylacetate, dichloromethane, methyl tert-butyl ether (MTBE), combinations thereof, or other suitable solvents or solvent mixtures) and an aqueous phase (e.g., an acidic solution such as a hydrochloric acid solution). The organic phase can be concentrated, and a suitable solvent can be added, e.g., MTBE, sequentially any number of times (e.g., 1, 2, 3, 4, or 5 or more times). In some embodiments, a method described herein can further include: (i) combining a compound of Formula (I) and isopropylacetate; (ii) conducting a first crystallization that can include tert-butyl methyl ether; and (iii) optionally, conducting a second crystallization that can include tert-butyl methyl ether. In other embodiments, a method described herein can further include: (i) conducting a first crystallization that can include tert-butyl methyl ether; and (ii) optionally, a second recrystallization using a solvent that can include tert-butyl methyl ether. In still other embodiments, a method described herein can further include: (i) combining a compound of Formula (I) and ethyl acetate; (ii) conducting a first crystallization that can include tert-butyl methyl ether; and (iii) optionally, conducting a second crystallization that can include tert-butyl methyl ether. In some embodiments described herein, including those of this paragraph, a method can further include the use of seed crystals of the compound of Formula (I)(ii) to assist in crystallization (for example, during at least one of the first crystallization and the second crystallization). In some embodiments, a method described herein can include (i) combining ethyl acetate and a compound of Formula (I); and (ii) conducting a crystallization that can include MTBE and seed crystals of a compound of Formula (I)(ii).

In some embodiments described herein, including those of the previous paragraph, a method can further include heating and then cooling (such as during a crystallization, including, at least one of the first crystallization and the second crystallization). The heating can take place at any suitable temperature, for example, a temperature suitable to dissolve a compound of Formula (I) in the solvent(s). The heating can also take place for an appropriate time. In some embodiments, the heating can take place at a temperature in the range of between about 30° C. to about 60° C. (for example, about 30° C. or about 50° C.). In some embodiments, the heating can take place for a time in the range of about 1 hour to about 6 hours. Likewise, the cooling can taking place for an appropriate time and at a temperature sufficient to allow either the desired compound or one or more impurities to fall out of the solvent(s). In some embodiments, including those of this and the previous paragraph, the cooling can takes place at a temperature in the range of between about −5° C. to about 10° C. (such as about 0° C.). In some embodiments, the cooling can takes place for a time in the range of about 1 hour to about 3 hours. In some embodiments, when the method includes multiple crystallizations, the mixture can be filtered between one or more of the crystallizations.

In some embodiments, the organic phase can be in an amount in the range of about 10 mL to about 1000 mL. In some embodiments, the organic phase can be in an amount in the range of about 20 mL to about 40 mL. In other embodiments, the organic phase can be in an amount in the range of about 100 mL to about 800 mL. In some embodiments, the solvent for crystallization (for example, MTBE) can be in an amount in the range of about 30 mL to about 750 mL. In some embodiments, the solvent for crystallization (for example, MTBE) can be in an amount in the range of about 50 mL to about 150 mL. In other embodiments, the solvent for crystallization (for example, MTBE) can be in an amount in the range of about 400 mL to about 600 mL. In other embodiments, the suitable solvent for dissolving the residue (for example, MTBE) can be in an amount of about 500 mL.

The diastereomeric ratio of a compound of Formula (I)(i) to a compound of Formula (I)(ii) obtained from a method described herein can vary. In some embodiments, a method described herein can provide a diastereomeric mixture with a diastereomeric ratio of 1:1 of a compound of Formula (I)(ii) to a compound of Formula (I)(i) (a compound of Formula (I)(ii):a compound of Formula (I)(i)). In other embodiments, a method described herein can provide a mixture of a compound of Formula (I)(i) and a compound of Formula (I)(ii) that is diastereomerically enriched in the compound of Formula (I)(ii). In some embodiments, a method described herein can provide a diastereomeric mixture of a compound of Formula (I)(i) and a compound of Formula (I)(ii) that is a diastereomeric mixture with a diastereomeric ratio of 1.5 or more:1 of a compound of Formula (I)(ii) to a compound of Formula (I)(i) (a compound of Formula (I)(ii):a compound of Formula (I)(i)). In some embodiments, a method described herein can provide a diastereomeric mixture with a diastereomeric ratio of 1.7 or more:1 of a compound of Formula (I)(ii) to a compound of Formula (I)(i) (a compound of Formula (I)(ii):a compound of Formula (I(i)). In some embodiments, a method described herein can provide a diastereomeric mixture of a compound of Formula (I)(i) and a compound of Formula (I)(ii) that a diastereomeric mixture with a diastereomeric ratio of 2.0 or more:1 of a compound of Formula (I)(ii) to a compound of Formula (I)(i) (a compound of Formula (I)(ii):a compound of Formula (I)(i)). In some embodiments, a method described herein can provide a diastereomeric mixture of a compound of Formula (I)(i) and a compound of Formula (I)(ii) that is a diastereomeric mixture with a diastereomeric ratio of 2.1 or more:1 of a compound of Formula (I)(ii) to a compound of Formula (I)(i) (a compound of Formula (I)(ii):a compound of Formula (I)(i)). In other embodiments, a method described herein can provide a mixture of a compound of Formula (I)(i) and a compound of Formula (I)(ii) that is diastereomerically enriched in the compound of Formula (I)(i). In some embodiments, a method described herein can provide a diastereomeric mixture with a diastereomeric ratio of a compound of Formula (I)(i) and a compound of Formula (I)(ii) that is 1:1.5 or more, 1:1.7 or more or 1:2.0 or more of a compound of Formula (I)(ii) to a compound of Formula (I)(i) (a compound of Formula (I)(ii) to a compound of Formula (I)(i)).

In some embodiments, a method described herein, including those described previously, can result in a mixture wherein the obtained compound of Formula (I)(ii) can be diastereomerically enriched by >90% (eq. of the compound of Formula (I)(ii)/(total eq. of the compound Formula (I)(i)+total eq. of the compound of Formula (I)(ii)). In some embodiments, a method described herein, including those described previously, can result in a mixture wherein the obtained compound of Formula (I)(ii) can be diastereomerically enriched by >95% (eq. of the compound of Formula (I)(ii)/(total eq. of the compound Formula (I)(i)+total eq. of the compound of Formula (I)(ii)). In some embodiments, a method described herein, including those described previously, can result in a mixture wherein the obtained compound of Formula (I)(ii) can be diastereomerically enriched by >98% (eq. of the compound of Formula (I)(ii)/(total eq. of the compound Formula (I)(i)+total eq. of the compound of Formula (I)(ii)). In some embodiments, a method described herein, including those described previously, can result in a mixture wherein the obtained compound of Formula (I)(ii) can be diastereomerically enriched by >99% (eq. of the compound of Formula (I)(ii)/(total eq. of the compound Formula (I)(i)+total eq. of the compound of Formula (I)(ii)).

One advantage of using a method described herein is that a compound of Formula (I) can be purified to obtain a compound of Formula (I)(ii) and/or a compound of Formula (I)(i) without the use of silica gel, and/or without having to switch solvent(s) in a second crystallization step. Thus, the overall yield of a compound of Formula (I)(ii) and/or a compound of Formula (I)(i) can be increased compared to a method that uses silica gel and/or a different solvent(s) in a second crystallization step. The crystallization procedure can be also scaled-up as desired for the production of larger amounts of product (such as a compound of Formula (I)(ii)).

When the compound of Formula (I) is obtained as a mixture of diastereomers of a compound of Formula (I)(i) and a compound of Formula (I)(ii), the diastereomers can be separated using methods know to those skilled the art. In some embodiments, a portion of the compound of Formula (I)(i) can be separated from the diastereomeric mixture of a compound of Formula (I)(i) and a compound of Formula (I)(ii) by supercritical fluid chromatography. In other embodiments, a portion of the compound of Formula (I)(i) can be separated from the diastereomeric mixture of a compound of Formula (I)(i) and a compound of Formula (I)(ii) by recrystallization. By separating a compound of Formula (I)(i) and a compound of Formula (I)(ii), the product can become diastereometrically enriched in one of the diastereomers, for example the product can become diastereometrically enriched in a compound of Formula (I)(ii).

In some embodiments, the compound of Formula (I) can be separated into its diastereomers of a compound of Formula (I)(i) and a compound of Formula (I)(ii) using Supercritical Fluid Chromatography (SFC) utilizing carbon dioxide in a liquid state as the mobile phase, wherein the compound of Formula (I) can be dissolved in a suitable solvent, e.g., methanol, ethanol, isopropanol, acetonitrile, or chloroform. In some embodiments, the solvent for a compound of Formula (I) can be methanol. SFC separation methods are described in Craig White and John Burnett (13 May 2005), "Integration of supercritical fluid chromatography into drug discovery as a routine support tool: II. Investigation and evaluation of supercritical fluid chromatography for achiral batch purification," *Journal of Chromatography A* 1074: 175-185.

In other embodiments, diastereomers of a compound of Formula (I) (such as a compound of Formula (I)(i) and a compound of Formula (I)(ii)) can be separated via recrystallization. In a single solvent recrystallization, the diastereomeric mixture of Formula (I) can be dissolved in an amount of solvent (for example, the smallest amount of solvent) necessary to fully dissolve the mixture, making a saturated solution. In some embodiments, the temperature of the solvent can be above room temperature. The solution can then be allowed to cool, resulting in one of the diastereomers recrystallizing from solution. The crystals comprising the desired diastereomer can be collected by filtration and the filtrate can be discarded. Alternatively, the filtrate can be retained and evaporated to obtain the desired diastereomer. In a multi-solvent recrystallization, two or more solvents can be used, with a second solvent slowly being added to a first solvent containing the dissolved diastereomeric mixture. Upon the addition of the second solvent, one of the diastereomers can crystallize from solution. In some embodiments, a portion of the compound of Formula (I)(i) can be separated from the diastereomeric mixture of a compound of Formula (I)(i) and a compound of Formula (I)(ii) via recrystallization using a multi-solvent system that can include dichloromethane and/or ethyl acetate in combination with MTBE; and optionally, seed crystals of a compound of Formula (I)(ii).

Separation of the diastereomers of a compound of Formula (I) can provide various ratios of a compound of Formula (I)(i) and a compound of Formula (I)(ii). In some embodiments, one or more of the separation techniques described herein can result in a mixture wherein the obtained compound of Formula (I) is diastereomerically enriched in the compound of Formula (I)(ii). In some embodiments, one or more of the separation techniques described herein can result in a mixture wherein the obtained compound of Formula (I)(ii) can be diastereomerically enriched by >95% (eq. of the compound of Formula (I)(ii)/(total eq. of the compound Formula (I)(i)+total eq. of the compound of Formula (I)(ii)). In some embodiments, one or more of the separation techniques described herein can result in a mixture wherein the obtained compound of Formula (I)(ii) can be diastereomerically enriched by >98% (eq. of the compound of Formula (I)(ii)/(total eq. of the compound Formula (I)(i)+total eq. of the compound of Formula (I)(ii)). In some embodiments, one or more of the separation techniques described herein can result in a mixture wherein the obtained compound of Formula (I)(ii) can be diastereomerically enriched by >99% (eq. of the compound of Formula (I)(ii)/(total eq. of the compound Formula (I)(i)+total eq. of the compound of Formula (I)(ii)).

In some embodiments, one or more of the separation techniques described herein can result in a mixture wherein the obtained compound of Formula (I) is diastereomerically enriched in the compound of Formula (I)(i). In some embodiments, one or more of the separation techniques described herein can result in a mixture wherein the obtained compound of Formula (I)(i) can be diastereomerically enriched by >90% (eq. of the compound of Formula (I)(i)/(total eq. of the compound Formula (I)(i)+total eq. of the compound of Formula (I)(ii)). In some embodiments, one or more of the separation techniques described herein can result in a mixture wherein the obtained compound of Formula (I)(i) can be diastereomerically enriched by >98% (eq. of the compound of Formula (I)(i)/(total eq. of the compound Formula (I)(i)+total eq. of the compound of Formula (I)(ii)). In some embodiments, one or more of the separation techniques described herein can result in a mixture wherein the obtained compound of Formula (I)(i) can be diastereomerically enriched by >99% (eq. of the compound of Formula (I)(i)/(total eq. of the compound Formula (I)(i)+total eq. of the compound of Formula (I)(ii)).

Various methods are known to those skilled in the art for isolating the final compound (for example, a compound of Formula (I)(ii)). In some embodiments, the final compound can be isolated by filtration.

Some embodiments described herein relate generally to a method of preparing a compound of Formula (B) that can include reacting O-phenylphosphorodichloridothioate with (S)-isopropyl 2-aminopropanote methanesulfonic acid. If desired, a base can be used in the reaction that provides a compound of Formula (B). Various suitable bases are described herein (for example, an amine base, an optionally substituted pyridine, or an optionally substituted imidazole). In some embodiments, the base can be triethylamine. The reaction that provides a compound of Formula (B) can be conducted in one or more solvents, or a mixture of solvents. In some embodiments, the solvent(s) can be non-polar solvent(s). Examples of non-polar solvents include, but are not limited to, hexane, benzene, toluene, 1,4-dioxane, chloroform, dichloromethane and diethyl ether.

EXAMPLES

Additional embodiments are disclosed in further detail in the following examples, which are not in any way intended to limit the scope of the claims.

Example 1

Preparation of L-alanine isopropyl ester derived 1-phenyloxy-chlorophosphothioate (2)

The compound 2 can be prepared according to the following reaction steps.

Step 1: Synthesis of 1-phenyloxydichlorophosphothioate reagent (1)

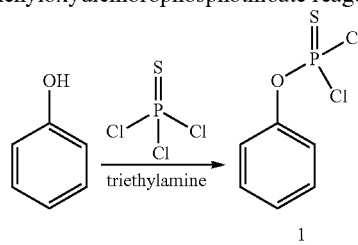

A 30 L glass reactor equipped with a mechanical stirrer (enamel), thermometer, dropping funnel and cooling batch was charged under argon atmosphere with dichloromethane (DCM) (16 L). Phosphorothioyl trichloride (1.613 L, 15.56 mol) was added under stirring, and the mixture cooled to −74° C. In a 10 L flask under argon, phenol (1.509 kg, 16.03 mol) was dissolved in DCM (2.8 L). The solution was cooled to 10° C. Triethylamine (2.200 L, 15.87 mol) was added. The solution was then transferred to the dropping funnel and added to the reactor at a rate that kept the internal temperature below −70° C. The resulting white suspension was stirred another 2 h at −70° C., then allowed to slowly warm to ambient temperature overnight. The suspension was transferred to a rotary evaporator and concentrated under vacuum (<80 mbar, $T_{bath}$=45° C.). The concentrate was diluted with tert-butyl methyl ether (MTBE) (6 L) and filtered over a glass-sinter Nutsch filter to remove ammonium salts. The salts were washed with TBME (4 L), and the filtrate was concentrated by rotary evaporation ($T_{bath}$=45° C.). The oil was dried on the rotavap for 5 h ($T_{bath}$=50° C., p<30 mbar). Crude compound 1 was obtained as a yellowish oil (3.442 kg). The crude product was purified by distillation via a short path (thin layer evaporator) using the following conditions: vacuum: 0.5 mbar, cooling rod: −15° C. and heating rod: +85° C. Purified compound 1 was obtained as a colorless liquid (2.75 kg).

Step 2: Synthesis of the L-alanine isopropyl ester derived 1-phenyloxy-chlorophosphothioate reagent (2)

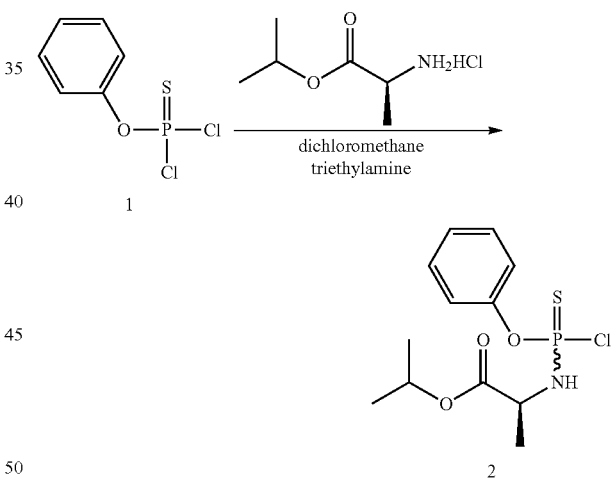

Method A

To a 30 L glass reactor equipped with a mechanical stirrer, thermometer, dropping funnel and cooling bath was added dichloromethane (10 L) under argon. A solution of O-phenylphosphorodichloridothioate (compound 1, 1600 g, 7.047 mol) dissolved in 2 L of dichloromethane was added. The resulting solution was cooled to −74° C., and triethylamine (2.002 L, 14.4 mol) was added at a rate to keep the internal temperature below −60° C. A solution of (S)-isopropyl 2-aminopropanote hydrochloride (1281 g, 7.64 mol) dissolved in 1.7 L of dichloromethane was added at a rate to keep internal temperature below −70° C. The resulting suspension was stirred at −70° C. for 30 min and then warmed to ambient temperature overnight.

The mixture was diluted with 5 L of methyl t-butyl ether, stirred for 1 h and then filtered. The cake was washed with 3 L of methyl t-butyl ether. The filtrate was concentrated under vacuum at 40° C. The crude product was dissolved in 1:1 dichloromethane and heptanes (12 L) and mixed with 5 kg of 60-200 μm mesh silica gel. The mixture was concentrated under vacuum. The adsorbed material was charged on top of a column packed with silica gel (5 Kg, 40-63 μm mesh) and eluted with 15 L of heptanes, 25 L of heptanes/ethyl acetate (98%:2%) and 52 L of heptanes/ethyl acetate (95%:5%). The collected fractions were concentrated in vacuum to give compound 2 (1503 g, 66%) of a colorless liquid.

Method B

To a 20 L jacketed reactor, equipped with reflux condenser, $N_2$ inlet, temperature controller, and thermocouple coupled with reaction monitoring software, was charged with (S)-isopropyl 2-aminopropanote hydrochloride (620.19 g, 3.70 mol, 1.05 eq), dichloromethane (8.0 L) and O-phenylphosphorodichloridothioate (compound 1, 800 g, 3.52 mol, 1.0 eq). The mixture was cooled to 0° C. Triethylamine (749 g, 7.40 mol, 2.1 eq) was added over 3 to 5 hr while maintaining the temperature at below 0° C. The mixture was stirred at 0° C. for 2 hr, warmed to 20° C. over a period of ~5 hr and stirred for 16 hr. A sample was tested using an in process control and conversion was shown to be 99.5%.

The mixture was concentrated to 2.4 to 3.2 L, and then charged with methyl t-butyl ether (8 L). The mixture was stirred for ~30 min. The slurry was filtered. The wet cake was washed with methyl t-butyl ether (1.6 L) to obtain a clear solution. The solution was filtered through a pad of silica gel and washed with methyl t-butyl ether (2.4 L). The combined organic solution was concentrated under vacuum to give compound 2 as a colorless oil (91%). The product was used in the next step without further purification.

Method C

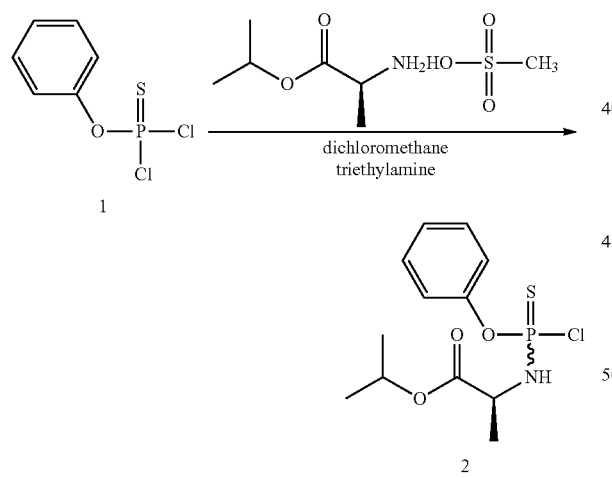

To a 100 mL jacketed reactor, equipped with reflux condenser, $N_2$ inlet, temperature controller, and thermocouple coupled with reaction monitoring software, was charged with (S)-isopropyl 2-aminopropanote methanesulfonic acid (1.73 g, 0.013 mol, 1.05 eq), dichloromethane (28.5 mL) and O-phenylphosphorodichloridothioate (compound 1, 2.85 g, 0.013 mol, 1.0 eq). The mixture was cooled to 0° C. Triethylamine (2.67 g, 2.1 eq) was added over 3 hr while maintaining the temperature below 0° C. The mixture was stirred at 0° C. for 2 hr, warmed to 20° C. over a period of 1 hr and stirred for 16 hr. A sample was tested using an in process control and conversion was shown to be 99.5%.

The mixture was concentrated to 9 to 12 mL, was charged methyl t-butyl ether (28.5 mL) and stirred for ~30 min. The slurry was filitered. The wet cake was washed with methyl t-butyl ether (6 mL) to obtain a clear solution. The solution was filtered through a pad of silica gel and washed with methyl t-butyl ether (9 mL). The combined organic solution was concentrated under vacuum to give compound 2 as a colorless oil (91%). The product was used in the next step without further purification.

Example 2

Preparation of 2'-C-methyluridine 5-(O-phenyl-N—(S)-1-(isopropoxycarbonyl)ethyl)thiophosphoramidate (3)

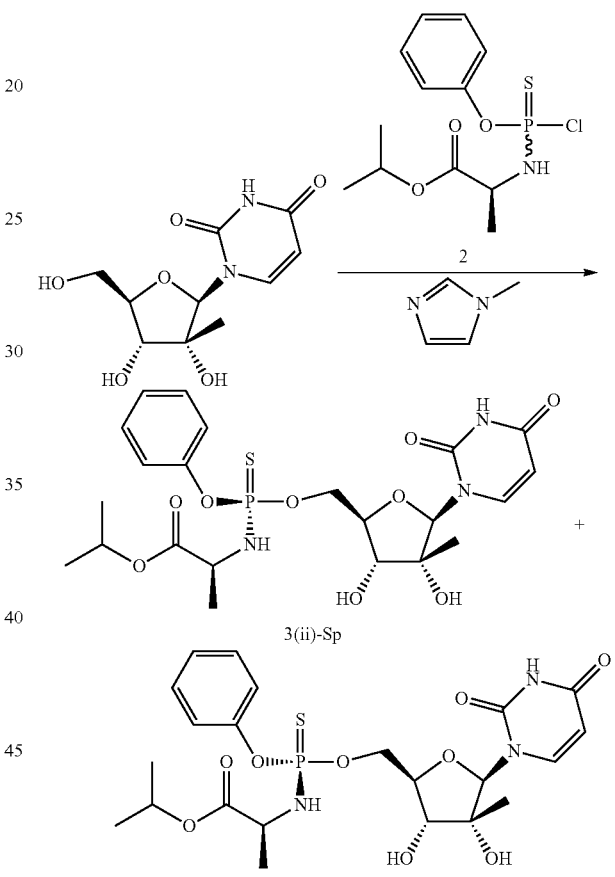

Method A

The starting material 2'-C-methyluridine (10.7 g, 41.5 mmol, 1 eq.) was dried by co-evaporation with pyridine (50 mL) twice and the residue was dried on high vacuum (approx. 0.5 mmHg) to dryness (approx. 15 min). The foamy semi-crystalline residue was dissolved in anhydrous acetonitrile (ACN; 60 mL) and N-methylimidazole (NMI; 17 mL, 207 mmol, 5 eq.). The resulting solution was cooled to 0° C. Compound 2 (15.4 g, 47.8 mmol, 1.15 eq.) was purified by chromatography and added dropwise in neat form over 15 minutes to the resulting solution. The mixture was stirred for one hour at 0° C., allowed to warm to room temperature, and left overnight. Thin layer chromatography (TLC; 15% methanol-DCM) indicated that the 2'-C-methyluridine was mostly consumed to yield compound 3.

The reaction was quenched with methanol (15 mL), stirred for 1 hr at room temperature, and concentrated under reduced pressure. The residue was taken into ethyl acetate (approx. 150 mL) and 2 N aqueous hydrochloric acid (80 mL) and the pH was adjusted to approx. 2 with 2 N hydrochloric acid. The organic phase was separated and washed sequentially with water (approx. 50 mL) and aqueous sodium bicarbonate (approx. 50 mL). The aqueous phases were back-extracted with ethyl acetate. The combined organic solution (approx. 200 mL) was dried over magnesium sulfate and filtered through a small silica gel pad (10 g of silica gel). More ethyl acetate (approx. 250 mL) was passed through the silica gel to elute the product. An in process control showed the diastereomeric ratio to be 1.68:1 of compound 3(ii)-Sp:compound 3(i)-Rp.

The solvent was removed under vacuum and the resulting foam was dissolved in MTBE (100 mL). The clear solution was seeded with 3(ii)-Sp crystals. The mixture was gently stirred using rotavap for 3 hours at room temperature (without vacuum) and then left in a refrigerator overnight. The precipitated solid was filtered off and rinsed with cold MTBE to provide 8.96 g (39.8% yield) of compound 3 as an off-white solid that had ~99% HPLC purity and was determined by chiral HPLC to be an 87:13 mixture of diastereomers compound 3(ii)-Sp:compound 3(i)-Rp. The obtained off-white solid of compound 3 was dissolved in DCM (30 mL; ethyl acetate can be used instead of DCM to obtain similar results) under reflux, the resulting solution was diluted with MTBE (60 mL), seeded with compound 3(ii)-Sp crystals and left for crystallization for 3 hours at room temperature and then overnight at 0° C. The crystalline solid was filtered off, washed with cold MTBE, and dried under vacuum overnight. The yield was 6.46 g (28.6%; uncorrected) of an off-white crystalline solid compound 3(ii)-Sp. HPLC 99% (compound 3(i)-Rp: 2% (chiral HPLC); residual MTBE ~5%).

Method B

To a 1.5 L Jacketed reactor, reflux condenser, $N_2$ inlet, temperature controller, and thermocouple coupled with reaction monitoring software, were charged 2'-C-methyluridine (50 g, 0.193 mol, 1 eq.), anhydrous acetonitrile (300 mL), and NMI (79.5 g, 0.968 mol, 5.0 eq.). After stirring the mixture for 30 min, it was cooled down to 0-5° C. Then, compound 2 (99.7 g, 0.309 mol, 1.6 eq.) was added dropwise into the solution over 0.5 hr. The mixture was stirred at 0° C. for 1 hr and warmed to 25° C. and stirred for 16 hr until HPLC showed 99% conversion. An in process control showed the diastereomeric ratio to be 1.75:1 of compound 3(ii)-Sp:compound 3(i)-Rp.

The reaction was quenched with MeOH (75 mL) and left to stir at 25° C. for 2 hr. The reaction mixture was concentrated to 150 to 175 mL, then isopropylacetate (IPAc) (500 mL) was charged, and the mixture was concentrated to 200 to 250 mL. The residue was partitioned between IPAc (750 mL) and 2N HCl (300 mL×2). The organic layer was separated and was washed with sat. aq. $NaHCO_3$ (250 mL) and water (250 mL).

The solution was concentrated to 150 to 200 mL and charged with MTBE (500 mL). The solution was again concentrated to 150 to 200 mL. The amount of IPAc in the residue was approx. 25 mL. MTBE (500 mL) was charged to the mixture and the mixture was stirred at 30° C. for 2 hr. The mixture was cooled to 0° C. and stirred for 4 hr., and filtered to give crude compound 3(ii)-Sp with 90% diastereomeric purity. The crude compound 3(ii)-Sp was slurried in MTBE (500 mL) at 50° C. for 2 hr. The mixture was then cooled to 0° C. and stirred for 2 hr., and filtered to give 36 g (35% yield) of a purified compound 3(ii)-Sp with 98% purity (compound 3(ii)-Rp: 2%).

Method C

A solution of 2'-methyluridine (50 g, 0.193 mol, 1 eq.) and N-methylimidazole (NMI) (79.5 g, 0.968 mol, 5.0 eq) in methyl isobutyl ketone (MIBK) (300 mL) was stirred at 0° C. Compound 2 (99.7 g, 0.309 mol, 1.6 eq) was added dropwise into the solution over 0.5 hr. The mixture was stirred at 0° C. for 5 hr, warmed to 2° C. and stirred for 16 hr until an in process control showed 95% conversion and a diastereomeric ratio to be 2.1:1 of compound 3(ii)-Sp:compound 3(i)-Rp.

The reaction was quenched by adding 2N HCl (300 mL) slowly and with stirring at 20° C. for 1 hr. The organic layer was separated and washed with 2N HCl (300 mL), 7% $NaHCO_3$ (300 mL), and water (250 mL).

The solution was concentrated to about 150 mL and charged with MTBE (500 mL). The mixture was warmed to 50° C., stirred for 1 hr, cooled to 0° C. over 1 hr and stirred for 4 hr. The solid was filtered to give the crude product with 95% purity and 4% diastereomer. The crude product was slurried in MTBE (500 mL) at 50° C. for 2 hr. The mixture was then cooled to 0° C., stirred for 2 hr and filtered to give the purified compound 3(ii)-Sp with 98% purity (compound 3(ii)-Rp: 2%). The solid was dried under vacuum at RT overnight to provide 40 g (38% yield) of 3(ii)-Sp.

Methods A, Methods B and C of Example 2 advantageously provide compound 3 with a greater selectivity to compound 3(ii)-Sp when compared to the method for preparing compound 3 described in U.S. Publication No. 2012/0071434, filed Sep. 19, 2011, which is hereby incorporated by reference for the limited purpose of its disclosure of the preparation of compound 3 in Example 3. A diastereomeric ratio of compound 3(ii)-Sp:compound 3(i)-Rp of 1.68:1, 1.75:1 and 2.1:1 was obtained from Method A of Example 2, Method B of Example 2 and Method C of Example 2, respectively, versus a diastereomeric ratio of 1:1 from Example 3 of U.S. Publication No. 2012/0071434 obtained prior to the separation via SFC or crystallization (Step 4: Separation of 3b(i)-Rp and 3b(ii)-Sp).

Example 4

Preparation of Compound (C)(i) and Compound (C)(ii)

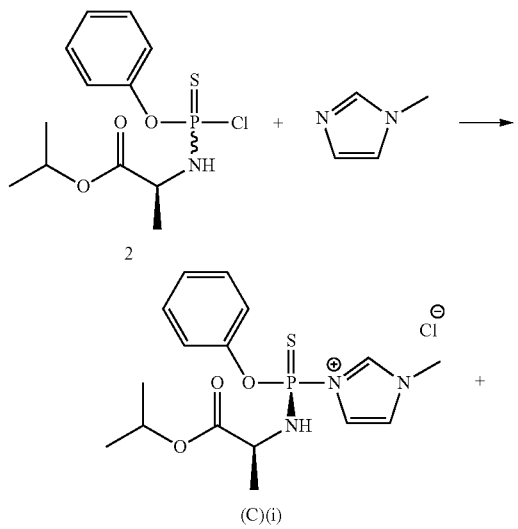

-continued

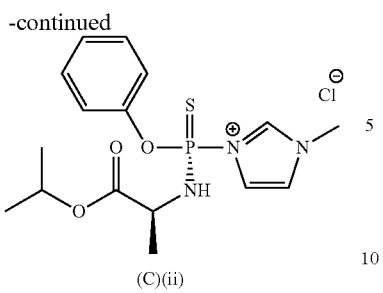

(C)(ii)

To a stirred solution of compound 2 (5 g, 15.6 mmol, 1 eq.) in acetonitrile (30 mL), was added NMI (1.3 g, 15.6 mmol) at 0° C. over 10 mins. The mixture was stirred at 0° C. for 30 mins, and then warmed to 25° C. and stirred for 30 mins. The reaction mixture was concentrated to give compounds (C)(i) and (C)(ii) (6.3 g, quantitative) as a mixture of two diastereomers with 2.3:1 ratio. The product was analyzed without further purification.

Figure 2:
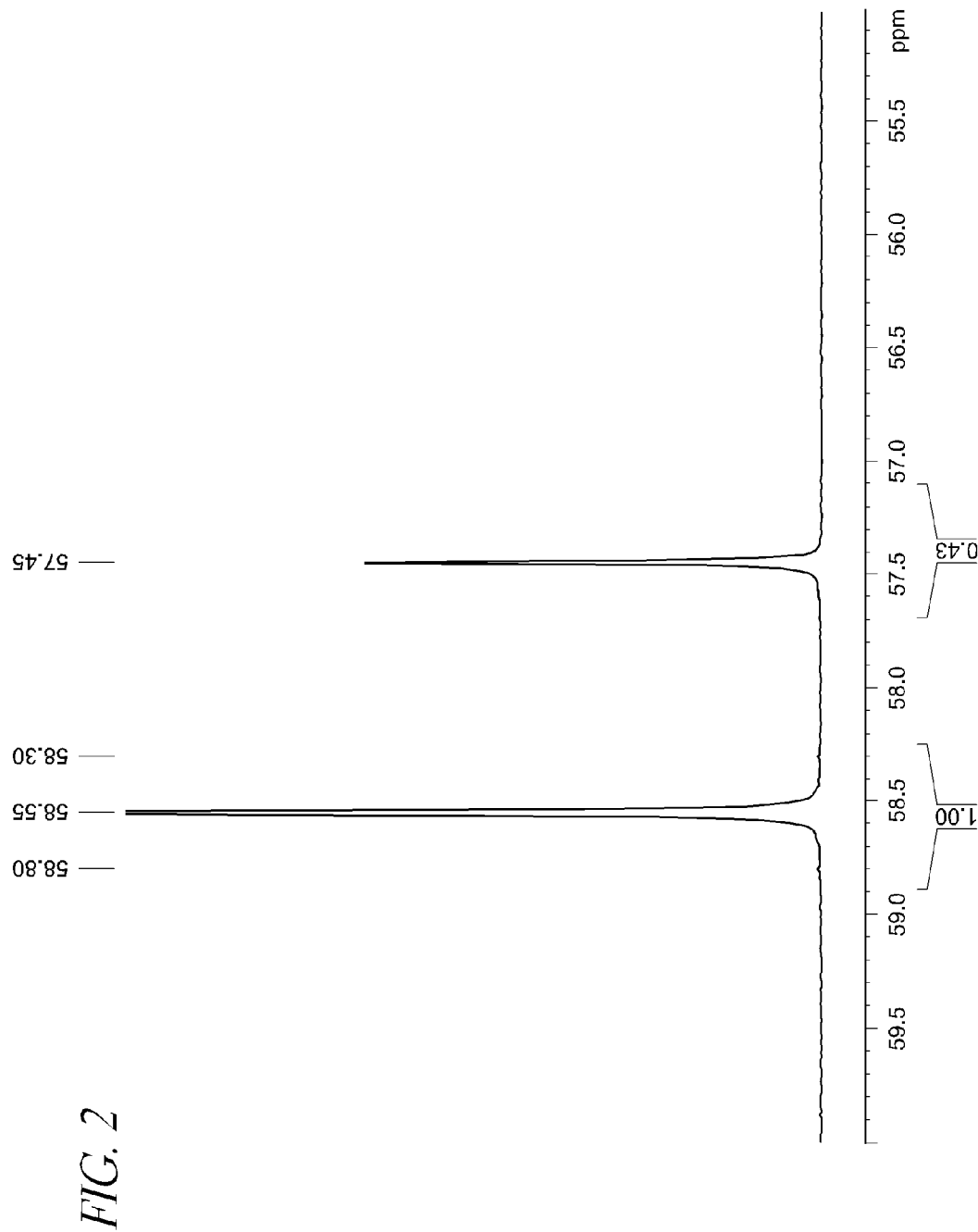
FIG. 2 shows $^{31}$P NMR spectrum of a diastereomeric mixture of compound (C)(i) and compound (C)(ii).
Figure 3A:
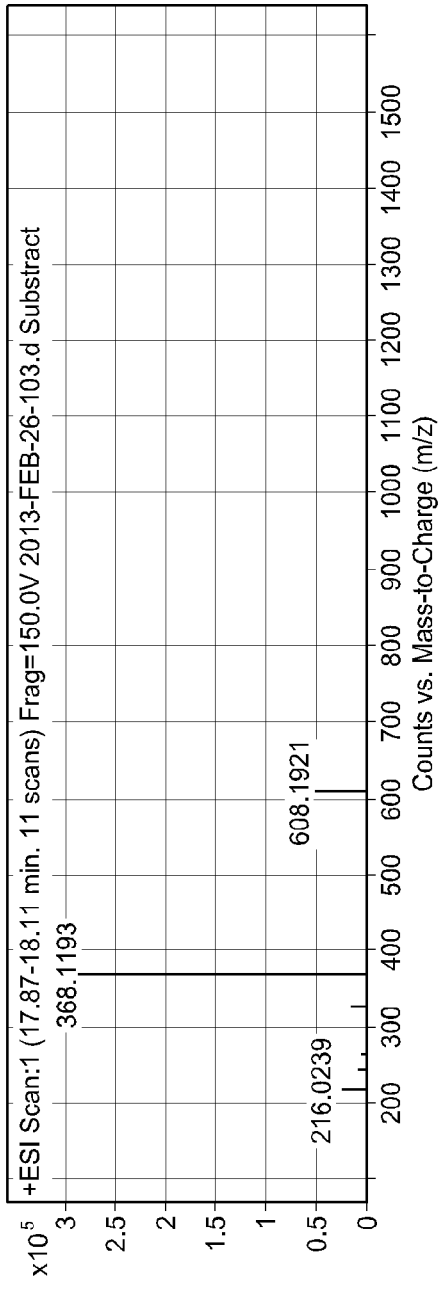
FIGS. 3A and 3B each show a LCMS spectra of a diastereomer selected from compound (C)(i) and compound (C)(ii).
Figure 3B:
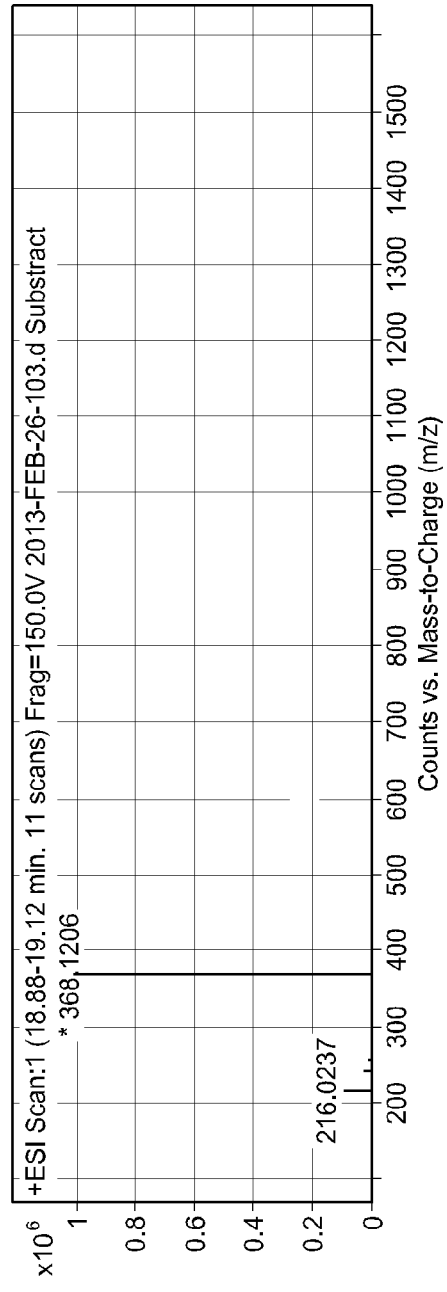

FIG. 1 shows $^1$H NMR spectrum of the product. $^1$H NMR (400 MHz, CD$_3$CN) δ 1.1-1.3 (6H, m), 1.4-1.6 (3H, m), 4.0 (3H, s), 4.1-4.3 (1H, m), 4.8-5.0 (1H, m), 7.2-7.5 (5H, m), 7.6 (1H, s), 8.5 (1H, m) and 9.9-10.0 (1H, m). FIG. 2 shows $^{31}$P NMR spectrum of the product. $^{31}$P NMR (162 MHz, decoupled, CD$_3$CN) δ 57.6 (s, minor diastereomer) and 58.7 (s, major diastereomer). The LCMS (ESI) spectra of the products are provided in FIGS. 3A and 3B: the mass of C$_{16}$H$_{23}$N$_3$O$_3$PS$^+$ was determined to be 368.118 (exact mass calculated is 368.12).

Although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:

1. A compound having the structure:

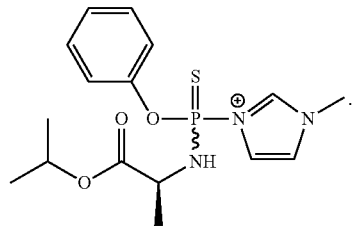 [SMILES: CC(C)OC(=O)[C@H](C)NP(=S)(Oc1ccccc1)[n+]1ccn(C)c1]

2. The compound of claim 1, wherein the counterion is a chloride anion.

3. The compound of claim 1 selected from:

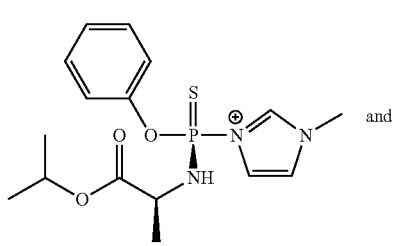

and

-continued

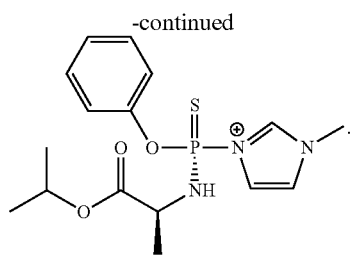

4. The compound of claim 3, wherein the counterion is a chloride anion.

5. A method of preparing the compound of claim 2 comprising:

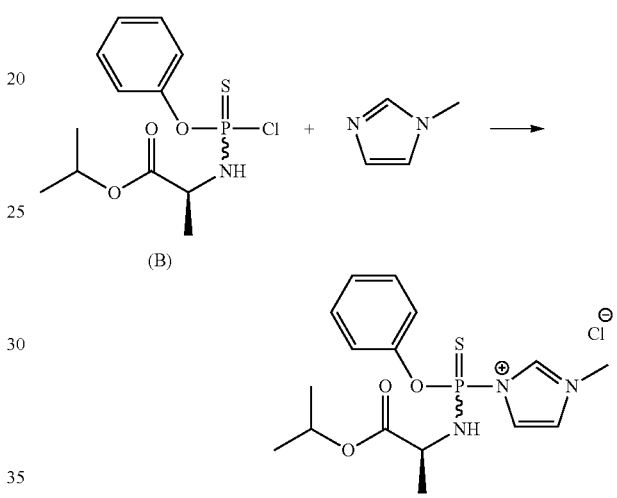

reacting a compound of Formula (B) with N-methyl imidazole (NMI).

6. The method of claim 5, wherein the amount of N-methyl imidazole is in excess compared to the amount of a compound of Formula (B).

7. The method of claim 5, wherein the amount of N-methyl imidazole to the amount of a compound of Formula (B) is >3 equivalents to 1 equivalent (>3 eq.:1 eq. of NMI:a compound of Formula (B)).

8. The method of claim 5, wherein the amount of N-methyl imidazole to the amount of a compound of Formula (B) is in the range of >2-5 equivalents to 1 equivalent (>2-5 eq.:1 eq. of NMI:a compound of Formula (B)).

9. The method of claim 5, wherein the amount of N-methyl imidazole to the amount of a compound of Formula (B) is 1 equivalent to 1 equivalent (1 eq.:1 eq. of NMI:a compound of Formula (B)).

10. The method of claim 5, wherein

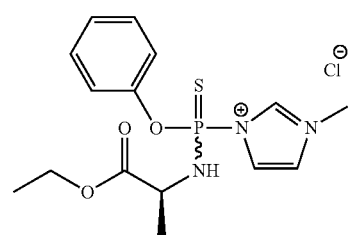

is diastereomerically enriched in

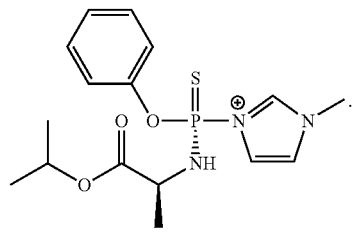 [SMILES: CC(C)OC(=O)[C@H](C)N[P@@](=S)(Oc1ccccc1)[n+]1ccn(C)c1]

11. The method of claim 5, further comprising a solvent.

12. The method of claim 11, wherein the solvent is a polar aprotic solvent.

13. The method of claim 12, wherein the polar aprotic solvent is acetonitrile.

14. The method of claim 12, wherein the polar aprotic solvent is methyl isobutyl ketone.

15. A method of preparing a compound of Formula (B) comprising:

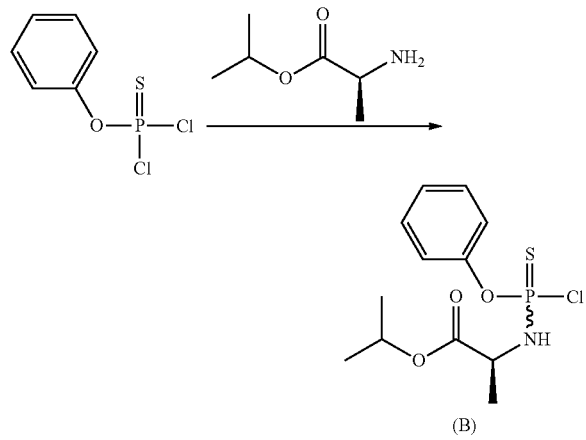

reacting O-phenylphosphorodichloridothioate with (S)-isopropyl 2-aminopropanote.

16. The method of claim 15, wherein the (S)-isopropyl 2-aminopropanote is a free base.

17. The method of claim 15, wherein the (S)-isopropyl 2-aminopropanote is a salt.

18. The method of claim 17, wherein the salt is a HCl salt.

19. A method of preparing a compound of Formula (I):

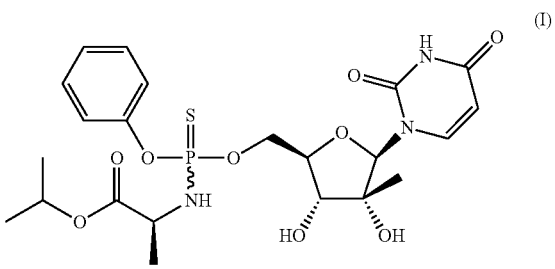 [SMILES: CC(C)OC(=O)[C@H](C)NP(=S)(OC[C@H]1O[C@@H](n2ccc(=O)[nH]c2=O)[C@](C)(O)[C@@H]1O)Oc1ccccc1]

wherein the method comprises:

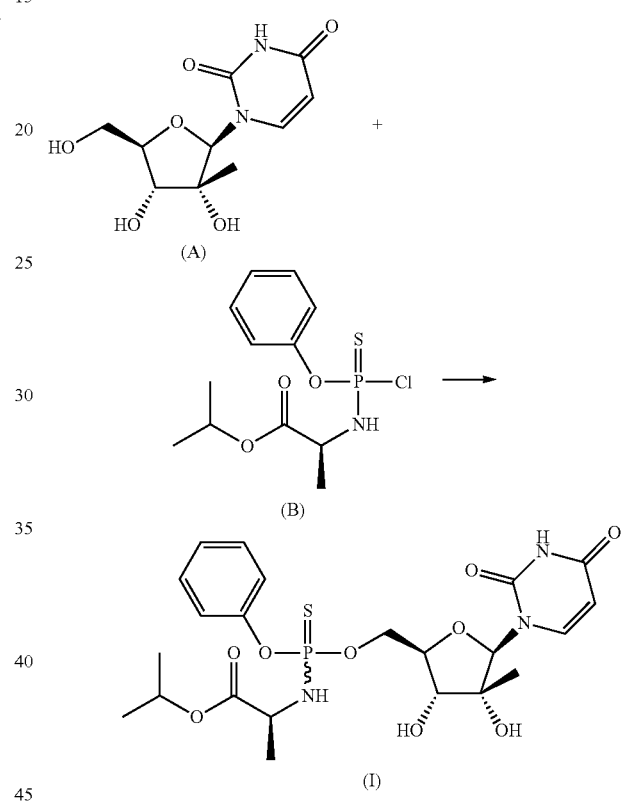

coupling a compound of Formula (A) and a compound of Formula (B) in a solvent, wherein the —OH groups and —NH group of the compound of Formula (A) are unprotected during the coupling reaction; and wherein the solvent is methyl isobutyl ketone.

20. The method of claim 17, wherein the salt is a methanesulfonic acid salt.

* * * * *

UNITED STATES PATENT AND TRADEMARK OFFICE
CERTIFICATE OF CORRECTION

PATENT NO. : 8,895,723 B2  
APPLICATION NO. : 13/845415  
DATED : November 25, 2014  
INVENTOR(S) : Vladimir Serebryany et al.

Page 1 of 1

It is certified that error appears in the above-identified patent and that said Letters Patent is hereby corrected as shown below:

In the Claims

In column 22 at line 44, In Claim 7, change ">3" to --≥3--.

In column 22 at line 45, In Claim 7, change "(>3" to --(≥3--.

In column 22 at line 49 (approx.), In Claim 8, change ">2-5" to --≥2-5--.

In column 22 at line 49 (approx.), In Claim 8, change ">2-5" to --(≥2-5--.

Signed and Sealed this  
Thirtieth Day of June, 2015

Michelle K. Lee  
*Director of the United States Patent and Trademark Office*